United States Patent
Despaux

(10) Patent No.: US 10,837,876 B2
(45) Date of Patent: Nov. 17, 2020

(54) GRANULAR SOLID SAMPLING DEVICE

(71) Applicant: AXENS, Rueil Malmaison (FR)

(72) Inventor: Yvan Despaux, Feucherolles (FR)

(73) Assignee: AXENS, Rueil Malmaison (FR)

( * ) Notice: Subject to any disclaimer, the term of this patent is extended or adjusted under 35 U.S.C. 154(b) by 186 days.

(21) Appl. No.: 16/060,097

(22) PCT Filed: Nov. 8, 2016

(86) PCT No.: PCT/EP2016/076937
§ 371 (c)(1),
(2) Date: Jun. 7, 2018

(87) PCT Pub. No.: WO2017/097524
PCT Pub. Date: Jun. 15, 2017

(65) Prior Publication Data
US 2018/0372594 A1   Dec. 27, 2018

(30) Foreign Application Priority Data

Dec. 10, 2015  (FR) ...................... 15 62153

(51) Int. Cl.
*G01N 1/08* (2006.01)
*G01N 1/20* (2006.01)
(Continued)

(52) U.S. Cl.
CPC ................. *G01N 1/08* (2013.01); *G01N 1/14* (2013.01); *G01N 1/20* (2013.01); *G01N 33/10* (2013.01);
(Continued)

(58) Field of Classification Search
CPC .. G01N 1/08; G01N 1/20; G01N 1/14; G01N 33/10; G01N 2001/1006; G01N 2001/1463; G01N 2033/0091; E21B 49/02
See application file for complete search history.

(56) References Cited

U.S. PATENT DOCUMENTS

| | | | | |
|---|---|---|---|---|
| 3,825,082 A | * | 7/1974 | Woodruff | ............... E21B 7/18 |
| | | | | 175/211 |
| 4,072,059 A | | 2/1978 | Hamilton | |

(Continued)

FOREIGN PATENT DOCUMENTS

| EP | 411932 A2 | 2/1991 |
|---|---|---|
| FR | 2679655 A1 | 1/1993 |
| WO | 2011035377 A1 | 3/2011 |

OTHER PUBLICATIONS

International Search Report PCT/EP2016/076937 dated Jan. 24, 2017.
(Continued)

*Primary Examiner* — Jonathan M Dunlap
(74) *Attorney, Agent, or Firm* — Millen White Zelano and Branigan, PC; Csaba Henter

(57) ABSTRACT

A device for the sampling and extraction of a granular solid in a pack of granular solids, containing a sampling probe (1), a sample collector (2) connected to said sampling probe (1), and a controller (3), the sampling probe (1) comprising a sampling tube (4) and at least one transfer tube (5), the sampling tube (4) and transfer tube (5) containing at least one central conduit and at least two lateral conduits, wherein the central conduit (6a) of the sampling tube (4) contains a collection chamber (10) containing a system (11) for retaining the granular solid, and the lateral conduits (7a, 7b) of the sampling tube (4) and transfer tube (5) are connected to a source of gaseous fluid (12) which is capable of extracting
(Continued)

the granular solid retained in the collection chamber (10) via the lateral conduits (8*a*, 8*b*) of the sampling tube (4) and transfer tube (5).

14 Claims, 2 Drawing Sheets

(51) Int. Cl.
    *G01N 1/14*     (2006.01)
    *G01N 1/10*     (2006.01)
    *G01N 33/10*     (2006.01)

(52) U.S. Cl.
    CPC ................ *G01N 2001/1006* (2013.01); *G01N 2001/1463* (2013.01)

(56) References Cited

U.S. PATENT DOCUMENTS

| | | | | |
|---|---|---|---|---|
| 4,088,025 | A | * | 5/1978 | Foster ............... G01N 1/08 73/863.33 |
| 4,283,946 | A | * | 8/1981 | Bowser ............. G01N 1/08 73/864.31 |
| 4,936,153 | A | * | 6/1990 | Klit ..................... G01N 1/08 406/175 |
| 5,211,062 | A | | 5/1993 | Moser |
| 2019/0234837 | A1 | * | 8/2019 | Van Berkel ............ G01N 1/24 |

OTHER PUBLICATIONS

Gorshteyn A Y et al: "Subsurface Detection of Environmental Pollutants", Instrumentation Science & Technology, Taylor & Francis Inc, US, vol. 27, No. 2, Apr. 1, 1999 (Apr. 1, 1999), pp. 111-121.

* cited by examiner

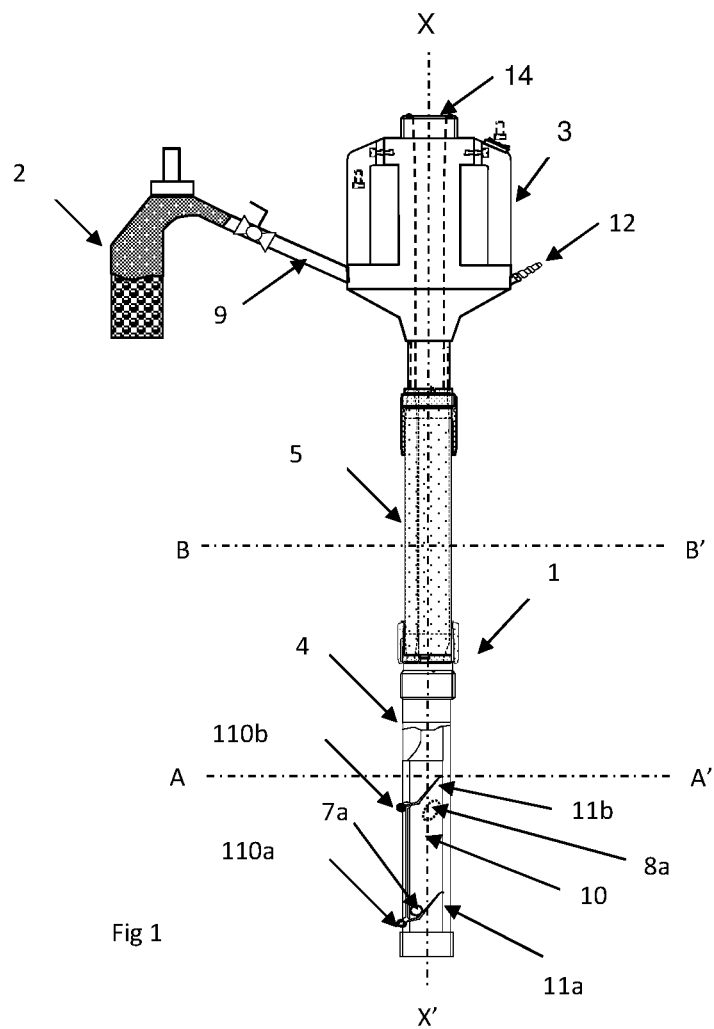
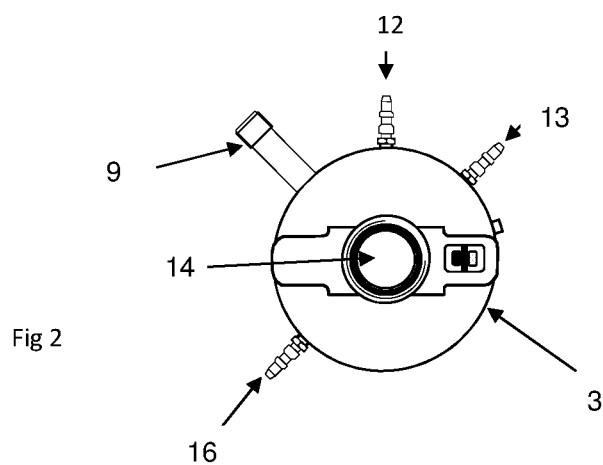

GRANULAR SOLID SAMPLING DEVICE

TECHNICAL FIELD OF THE INVENTION

The present invention relates to a device for the sampling and extraction of granular solids, as well as to a method for carrying out such an extraction.

PRIOR ART

Devices for the sampling and extraction of granular solids, for example in a pack of granular solids (also known as a bed of granular solids) distributed in a vessel, are known in the prior art.

The document FR 2 679 655 describes a sampling probe for the sampling and extraction of loose granular solids by core sampling and aspiration of said granular solids. The sampling probe is constituted by three juxtaposed conduits, a central conduit and two lateral conduits, in which three streams of air move as counter-currents. In that device, the gas streams moving in the lateral tubes act to equilibrate the turbulences which are generated when aspirating the granular solids into the central tube.

The document EP 0 411 932 describes a pneumatic sampling probe for extracting a sample which is representative of a loose material. The wall of the probe comprises an opening for withdrawing the sample which is aspirated by means of a vacuum pump. Next, compressed air is injected in order to stop the sampling and transport the sample to a storage zone. The inner portion of the end of the zone, which is rounded, comprises an intermediate storage zone for the sample. However, that device is not suitable for the extraction of granular solids located at a depth of more than one or two metres, for example in a silo or in a bed of catalyst or adsorbent contained in a reactor.

The document U.S. Pat. No. 4,072,059 describes a device comprising a sampling probe comprising a plurality of sampling openings located at different levels on the probe, as well as suction means connected to said openings in order to withdraw samples from a pack of granular solids. Again, a device of that type cannot be used to sample depths beyond two metres or even less, as the device has to be driven into a pack of granular solids using only human strength. Thus, as with the device disclosed in the document EP 0 411 932, it is necessary to partially empty the silo or reactor containing the bed of catalyst or the adsorbent by an amount of one or two metres in order to sample at a plurality of depths.

The device in accordance with the invention can be used to overcome the disadvantages of prior art devices by proposing a device for the sampling and extraction of granular solids located in a pack of granular solids, meaning that samples can be taken at different depths in the pack without the need to carry out any intermediate operation involving emptying part of the granular solids constituting the pack, and also preserving the physico-chemical integrity of said granular solid.

The device in accordance with the invention can be used to sample small quantities of granular solids (20 to 200 cm$^3$), and therefore in a limited zone and with good precision, which means that the state of the granular solid in these various zones can be determined. This means that the state of a granular solid can easily be inspected, or reasons for any degradation thereof can be determined by analysis of these localized samples.

The device in accordance with the invention can be used to inspect the quality of granular solids and/or their physico-chemical properties, such as, for example, in cereals (wheat, corn, rape, rice) stored in silos, sand, grit, charcoal, cements or other solid materials the quality of which is to be inspected. The device in accordance with the invention may be used to detect any deterioration in the quality of cereal grains in storage vessels.

The device in accordance with the invention is thus of particular application in the detection of poisons of catalysts or of solid adsorbents which cause their performance to deteriorate. It can be used to determine the extent of the zone of a bed of catalyst or of an adsorbent involved in that poisoning.

As an example, the device in accordance with the invention may also be used to verify proper functioning of an adsorbent by taking local samples and analysing them, which means that a check can be carried out that the products to be adsorbed are being effectively retained by said adsorbent.

OBJECTIVES OF THE INVENTION

In a first aspect, the invention concerns a device for the sampling and extraction of at least one granular solid in a pack of granular solids, said device comprising a sampling probe, a sample collector connected to said sampling probe, and a control means, said sampling probe comprising a sampling tube which is capable of extracting said granular solid from said pack, said sampling tube being connected to at least one transfer tube which is capable of transferring said extracted granular solid via said sampling tube to the sample collector, said sampling tube and said transfer tube each comprising at least one central conduit and at least two lateral conduits, said central conduit and said lateral conduits of said sampling tube being respectively connected to the central conduit and to the lateral conduits of said transfer tube, said central conduit of said sampling tube additionally being connected to the lateral conduits of said sampling tube;

characterized in that said central conduit of said sampling tube comprises a collection chamber comprising a system for retaining said granular solid, and in that said lateral conduits of said sampling tube and transfer tube are connected to a source of gaseous fluid which is capable of extracting said granular solid retained in the collection chamber via the lateral conduits of said sampling tube and transfer tube.

Preferably, said system for retaining the sampling tube is in the form of a system with two flaps disposed either side of the collection chamber.

Advantageously, the distance between the two flaps is in the range 100 to 400 mm.

Preferably, the two flaps are pivoted on their lower edge.

Advantageously, said central conduits of said sampling tube and transfer tube are connected to a source of gaseous fluid.

Preferably, said gaseous fluid control means is capable of generating a partial vacuum in the central conduits of said sampling tube and transfer tube.

Preferably, said transfer tubes have a length in the range 200 to 900 mm.

Preferably, said transfer tubes have a diameter in the range 25 to 70 mm.

Advantageously, said device comprises in the range 1 to 30 transfer tubes.

Preferably, said sampling tube and transfer tube each comprise a supplemental lateral conduit.

Advantageously, said supplemental lateral conduits of said sampling tube and transfer tube are connected to a source of gaseous fluid.

Preferably, the volume of the collection chamber is in the range 20 to 200 cm³.

In another aspect, the invention concerns a method for sampling and extracting at least one granular solid by means of a device in accordance with the invention, comprising the following steps:

a) inserting said sampling probe into a pack of granular solids to a predetermined depth;

b) extracting at least one granular solid from the pack and retaining it in the collection chamber of said sampling tube by means of a retaining system;

c) injecting a gaseous fluid under pressure into the lateral conduits of said sampling tube and transfer tube in order to extract said granular solid which has been extracted and retained in step b);

d) recovering said granular solid in said sample collector.

In another aspect, the invention concerns the use of a device in accordance with the invention for the sampling and extraction of at least one granular solid selected from the following group of granular solids: grains of catalyst, cereals, sand, grit, charcoal, and cements.

BRIEF DESCRIPTION OF THE DRAWINGS

FIG. 1 is a longitudinal sectional view of the device in accordance with the invention (a single transfer tube 5 is shown in FIG. 1), comprising a sampling probe 1, a sample collector 2 and a control means 3, said sampling tube 4 comprising a collection chamber 10 comprising a retaining system 11 in the form of a system with two flaps 11a, 11b.

FIG. 2 is a top view of the device in accordance with the invention, in which the inlets and outlets for the gaseous fluids are shown.

DETAILED DESCRIPTION OF THE INVENTION

Figure 3A:
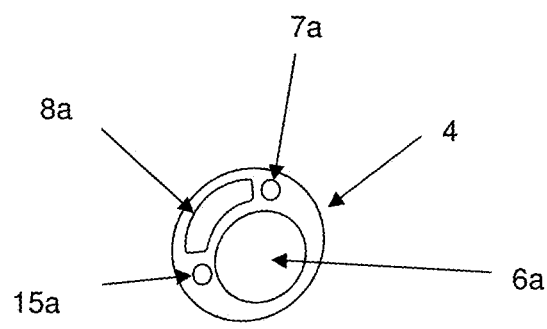
FIG. 3a is a cross-sectional view along the axis AA' shown in FIG. 1 of a sampling tube 4 of the device in accordance with the invention.

The invention will now be described with reference to FIGS. 1 to 4, which represent an embodiment of the device in accordance with the invention, and are provided by way of non-limiting example.

Referring to FIG. 1, the device in accordance with the invention comprises a sampling probe 1, a sample collector 2 and a control means 3, said sample collector 2 being connected to said sampling probe 1 via an outlet conduit 9 located on the control means 3. The sampling probe 1 comprises two distinct portions. The lower portion of the sampling probe 1 comprises a sampling tube 4; the upper portion of the sampling probe comprises at least one transfer tube 5. The sampling tube 4 functions to extract at least one granular solid which is in a pack; the transfer tube 5 functions to transfer the extracted granular solid via the sampling tube 4 to the sample collector 2.

Figure 4:
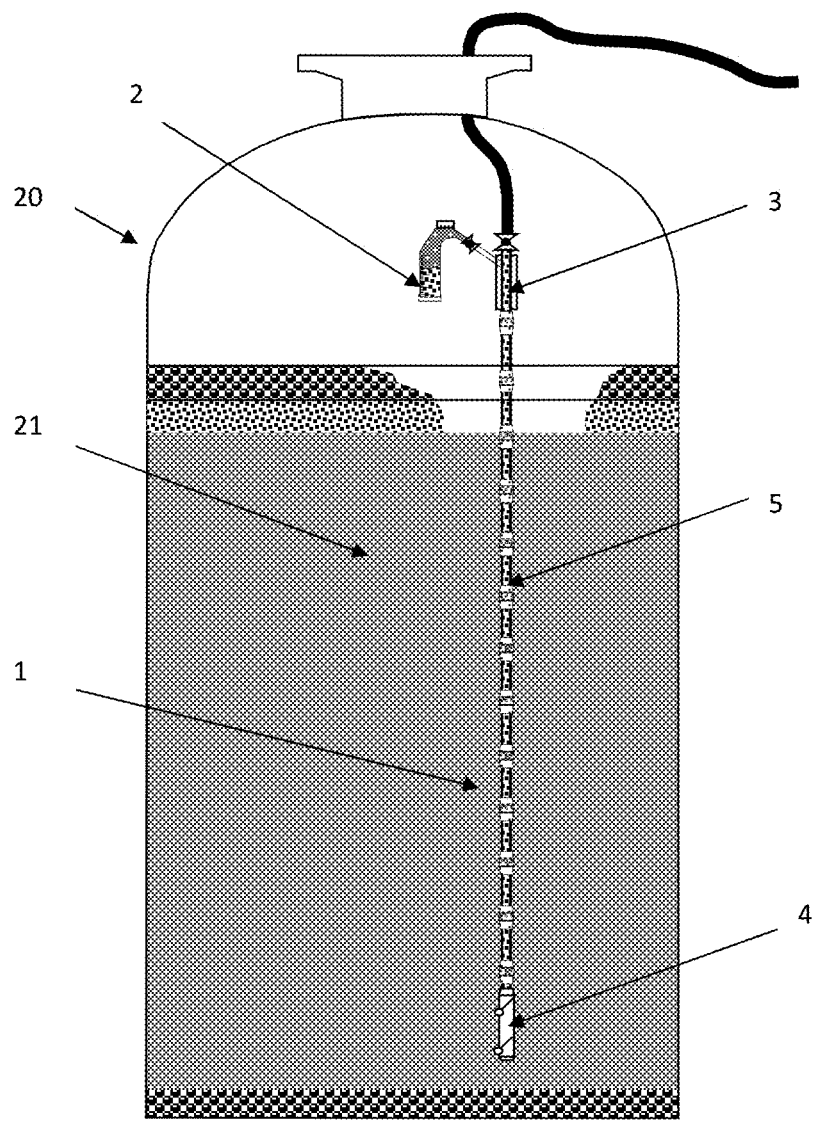
FIG. 4 illustrates a device in accordance with the invention in position in a reactor 20 comprising a pack of granular solids 21 in the form of grains of catalyst. The device in accordance with the invention comprises a sampling probe 1, a sample collector 2 and a control means 3, said sampling probe comprising a sampling tube 4 and a plurality of transfer tubes 5 (12 transfer tubes are shown in FIG. 4).

The sampling tube 4 and transfer tube 5 are divided into a plurality of conduits which are parallel and impermeable over their entire length. When assembling the device in accordance with the invention, the sampling tube 4 and transfer tube 5 are assembled progressively end to end by screwing them together and are dropped vertically or at an angle, for example into a catalytic bed (FIG. 4).

Figure 3B:
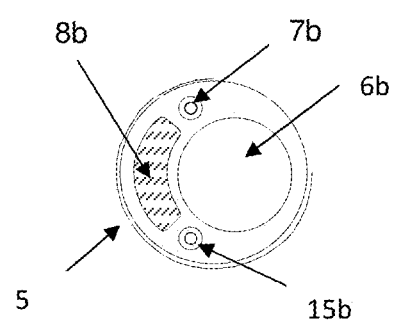
FIG. 3b is a cross-sectional view along the axis BB' shown in FIG. 1 of a transfer tube 5 of the device in accordance with the invention.

Referring to FIGS. 1, 3a and 3b, the sampling tube 4 comprises a central conduit 6a and two lateral conduits 7a, 8a and said transfer tube 5 comprises a central conduit 6b and two lateral conduits 7b, 8b. When the device in accordance with the invention is assembled and is in operation, the central conduit 6a of the sampling tube 4 is connected to the central conduit 6b of the transfer tube 5. Similarly, the lateral conduits 7a, 8a of the sampling tube 4 are respectively connected to the lateral conduits 7b, 8b of the transfer tube 5.

The sampling tube 4 comprises a collection chamber 10 (see FIG. 1) located in the central conduit 6a. This collection chamber 10 also comprises a retaining system 11 for retaining a granular solid extracted from a pack. The volume of the collection chamber 10 is in the range 20 to 200 cm³, preferably in the range 50 to 150 cm³. More particularly, the retaining system 11 is in the form of a system with two flaps 11a, 11b which operate by opening and closing simultaneously, for example with the aid of a pneumatic actuator or any other equivalent means. The flaps are pivoted about their lower edge 110a, 110b. Preferably, the lower edges of the flaps 110a, 110b are fixed directly on the walls of the central conduit 6a of the sampling tube 4. The flaps 11a, 11b are disposed longitudinally on the sampling tube 4 along the axis AA', as can be seen in FIG. 1. Preferably, the distance between the two flaps 11a, 11b is in the range 100 to 400 mm, preferably in the range 150 to 300 mm. The sampling tube 4 has a length in the range 200 to 900 mm, preferably in the range 300 to 800 mm, and a diameter in the range 25 to 70 mm, preferably 30 mm to 60 mm and more preferably 35 to 55 mm.

The number of transfer tubes 5 may vary widely as a function of the envisaged use, and in particular the desired analysis depth. Preferably, the number of transfer tubes 5 is in the range 1 to 30, and preferably in the range 1 to 20. The transfer tubes 5 have a length in the range 200 to 900 mm, preferably in the range 300 to 800 mm, and a diameter in the range 25 to 70 mm, preferably in the range 30 mm to 60 mm and more preferably 35 to 55 mm. In one particular embodiment of the invention, the upper portion and lower portion of each transfer tube 5 may each have a different diameter. Advantageously, the transfer tubes 5 are all identical and independent of each other.

The transfer tubes 5 are aligned vertically and are connected together. At least one transfer tube 5 is connected to the control means 3, and at least one transfer tube is connected to the sampling tube 4. In the particular embodiment in which a single transfer tube 5 is used, said transfer tube is connected to both the sampling tube 4 and to the control means 3.

The sampling tube 4 and transfer tube 5 may be connected together by screwing up tightly as the sampling probe 1 is dropped into the pack of granular solids. This means that the position of the point to be sampled at a predetermined depth can be reached. The lower portion of the control means 3 and the upper portion of the sampling tube 4 preferably have shapes and dimensions which are compatible with those of the transfer tubes 5 so that they can be connected together.

Advantageously, the control means 3 is capable of generating a partial vacuum in the central conduits 6a, 6b of said sampling tube 4 and transfer tube 5. The formation of a partial vacuum of gas in the central conduits 6a, 6b of said sampling tube 4 and transfer tube 5 facilitates dropping the device in accordance with the invention into the depths of the pack of granular solids.

In accordance with the invention, the lateral conduits 7a, 8a of the sampling tubes 4 and the lateral conduits 7b, 8b of the transfer tubes 5 are connected to a source of gaseous fluid 12, such as air or an inert gas, via the control means 3 (see FIG. 2), which is capable of extracting a granular solid when the latter is retained in the collection chamber 10 of the sampling tube 4, via the lateral conduits 8a then 8b of said sampling tube 4 and transfer tube 5.

In a particular embodiment of the invention, the device may further comprise a vibrating pneumatic tool (not shown in the figures), which acts to facilitate dropping and/or lifting the sampling probe 1 into a pack of granular solids. In particular, when the granular solids are grains of catalyst, penetration of the sampling probe 1 may be difficult due, for example, to coking of said catalyst or to partial agglomeration of said grains of catalyst. The vibrating pneumatic tool may be fixed directly to the sampling tube 4 and be supplied with a source of gaseous fluid 16, such as air or inert gas, passing through the control means 3 (see FIG. 2) then via the supplemental lateral conduits 15a and 15b of said sampling tube 4 and transfer tube 5 respectively (see FIGS. 3a and 3b). More particularly, the vibrating pneumatic tool may be in the form of two lateral pneumatic actuators (not shown in the figures).

The device in accordance with the invention may be used for the extraction or sampling of at least one granular solid in a pack of granular solids. In accordance with the invention, the method comprises at least the following steps:

a) inserting said sampling probe 1 into a pack of granular solids to a predetermined depth;

b) extracting at least one granular solid from the pack and retaining said granular solid in the collection chamber 10 of said sampling tube 4 by means of a retaining system 11;

c) injecting a gaseous fluid 12 under pressure, such as air or an inert gas, into the lateral conduits 7a, 7b of said sampling tube 4 and transfer tube 5 in order to extract said granular solid which has been extracted and retained in step b);

d) recovering said granular solid in said sample collector 2.

The steps of the method in accordance with the invention are described in detail below.

Step a)

The device in accordance with the invention is dropped progressively into a pack of granular solids by vacuum aspiration via the control means 3 for said granular solids passing through the central conduits 6a, 6b of the sampling tube 4 and transfer tube 5, at the same time with progressive manual pushing by the operator.

As the sampling probe 1 is dropped into the bed of granular solids, the retaining system 11 of the sampling tube 4 is not activated. When the retaining system 11 is in the form of a system with two flaps 11a and 11b, the two flaps are in the open position, i.e. the granular solids can move freely in the collection chamber 10 and the central channel 6a of the sampling tube 4.

By way of illustration, for sampling tubes 4 and transfer tubes 5 of 500 mm in length and 50 mm in diameter, approximately 1.5 litres of granular solids per metre of tubes 4 or 5 pass through the central conduits 6a and 6b of said sampling tube 4 and transfer tube 5 and are then evacuated from the device via the outlet 14 located on the control means 3. The outlet 14 may be connected to a vacuum (not shown in the figures) located externally of the reactor 20 (see FIG. 4), connected to the central channels 6a and 6b via the control means 3.

The sampling tube 4 and the transfer tubes 5 are assembled as the sampling probe 1 is dropped into the pack of granular solids. The rate of aspiration of the granular solids may be adjusted by means of a vacuum valve (not shown in the figures). The sampling probe 1 then drops into the pack of granular solids down to the predetermined depth.

Step b)

Step b) of the method in accordance with the invention consists of extracting and retaining at least one granular solid from the pack. Vacuum aspiration of the granular solids via the control means 3 is stopped and the retaining system 11 of the sampling tube 4 is activated. When the retaining system 11 is in the form of a system with two flaps 11a and 11b, said flaps are placed in the closed position; the granular solid included in the collection chamber 10 is retained in the sampling tube 4. The lower edges 110a and 110b of the flaps 11a and 11b, fixed on the wall of the central conduit 6a of the sampling tube 4, pivot about their axis of rotation, resulting in the flaps 11a and 11b passing from the vertical position to a horizontal position.

Maintenance of the flaps in the horizontal position may be improved by injecting a downwardly directed flow of gas 13, such as air or an inert gas, injected via the control means 3 (see FIG. 2) into the central conduits 6a and 6b of the sampling tube 4 and transfer tube 5.

In the closed position, the two flaps 11a and 11b hold the sample of granular solid. The sample of granular solid has a volume which is generally in the range 20 to 300 cm$^3$, preferably in the range 30 to 250 cm$^3$.

Step c)

Step c) of the method in accordance with the invention consists of sending the sample of granular solid retained in the collection chamber 10 to the sample collector 2. During this step, a gaseous fluid 12 under pressure, such as air or an inert gas, is injected into the lateral conduits 7a, 7b of said sampling tube 4 and transfer tube 5 in order to extract said granular solid which has been extracted and retained in step b). More particularly, the sample of granular solid is lifted towards the collector 2 by injecting a downflow of gaseous fluid 12 under pressure into the lateral conduits 7a and 7b of the sampling tube 4 and transfer tube 5, the lateral conduit 7a of the sampling tube 4 being connected to the central conduit 6a of said tube 4 above the base of the lower flap 11a. The gaseous fluid then pushes the sample of granular solid which enters the lateral conduit 8a of the sampling tube 4 the opening of which is located just below the upper flap 11b. The sample of granular solid moves in the lateral conduits 8a and 8b of the sampling tube 4 and transfer tube 5, which are tightly connected to the sample collector 2.

The method in accordance with the invention may also comprise supplemental steps, for example for carrying out a second extraction of a granular solid in the pack. After the step for extraction of at least one sample of granular solids, the sampling tube 4 and transfer tube 5 may be raised by placing the central conduits 6a and 6b of said tubes under pressure, simultaneously with manually forcing the sampling probe 1 upwards.

The device in accordance with the invention, as well as the method described above using such a device, is applicable to any type of granular solids such as, for example, cereals (wheat, corn, rape, rice) stored in silos, sand, grit, charcoal, cements or other solid materials where the quality of the granular solids and/or their physico-chemical properties are to be inspected. More particularly, the invention is applicable to sampling and/or extraction of granular solids of the grains of catalyst type disposed in a reactor, for example in a chemical reactor, with a view to carrying out different analyses and/or physico-chemical tests.

The invention claimed is:

1. A device for the sampling and extraction of at least one granular solid in a pack of granular solids, said device comprising a sampling probe (1), a sample collector (2) connected to said sampling probe (1), and a controller (3), said sampling probe (1) comprising a sampling tube (4) which is capable of extracting said granular solid from said pack, said sampling tube (4) being connected to at least one transfer tube (5) which is capable of transferring said extracted granular solid via said sampling tube (4) to the sample collector (2), said sampling tube (4) and said transfer tube (5) each comprising at least one central conduit and at least two lateral conduits, said central conduit (6a) and said lateral conduits (7a, 8a) of said sampling tube (4) being respectively connected to the central conduit (6b) and to the lateral conduits (7b, 8b) of said transfer tube (5), said central conduit (6a) of said sampling tube (4) additionally being connected to the lateral conduits (7a, 8a) of said sampling tube (4);

wherein said central conduit (6a) of said sampling tube (4) comprises a collection chamber (10) comprising a system (11) for retaining said granular solid, and in that said lateral conduits (7a, 7b) of said sampling tube (4) and transfer tube (5) are connected to a source of gaseous fluid (12) which is capable of extracting said granular solid retained in the collection chamber (10) via the lateral conduits (8a, 8b) of said sampling tube (4) and transfer tube (5).

2. The device as claimed in claim 1, wherein said system (11) for retaining the sampling tube (4) is in the form of a system with two flaps (11a, 11b) disposed either side of the collection chamber (10).

3. The device as claimed in claim 2, wherein the distance between the two flaps (11a, 11b) is in the range of 100 to 400 mm.

4. The device as claimed in claim 2, wherein the two flaps (11a, 11b) are pivoted on their lower edge (110a, 110b).

5. The device as claimed in claim 1, wherein said central conduits (6a, 6b) of said sampling tube (4) and transfer tube (5) are connected to a source of gaseous fluid (13).

6. The device as claimed in claim 1, wherein said gaseous fluid controller (3) is capable of generating a partial vacuum in the central conduits (6a, 6b) of said sampling tube (4) and transfer tube (5).

7. The device as claimed in claim 1, wherein said transfer tubes (5) have a length in the range of 200 to 900 mm.

8. The device as claimed in claim 1, wherein said transfer tubes (5) have a diameter in the range of 25 to 70 mm.

9. The device as claimed in claim 1, wherein said device comprises 1 to 30 transfer tubes (5).

10. The device as claimed in claim 1, wherein said sampling tube (4) and transfer tube (5) each comprise a supplemental lateral conduit.

11. The device as claimed in claim 10, wherein said supplemental lateral conduits of said sampling tube (4) and transfer tube (5) are connected to a source of gaseous fluid.

12. The device as claimed in claim 1, wherein the volume of the collection chamber (10) is in the range of 20 to 200 $cm^3$.

13. A method for sampling and extracting at least one granular solid by a device as claimed in claim 1, comprising:
  a) inserting said sampling probe (1) into a pack of granular solids to a predetermined depth;
  b) extracting at least one granular solid from the pack and retaining it in the collection chamber (10) of said sampling tube (4) by a retaining system (11);
  c) injecting a gaseous fluid (12) under pressure into the lateral conduits (7a, 7b) of said sampling tube (4) and transfer tube (5) in order to extract said granular solid which has been extracted and retained in step b); and
  d) recovering said granular solid in said sample collector (2).

14. A method as claimed in claim 13, which is for the sampling and extraction of at least one granular solid selected from the group consisting of the following granular solids: grains of catalyst, cereals, sand, grit, charcoal, and cements.

* * * * *